US012593866B2

(12) United States Patent
Campitelli et al.

(10) Patent No.: US 12,593,866 B2
(45) Date of Patent: Apr. 7, 2026

(54) HOLDER FOR INHALER ARTICLE

(71) Applicant: PHILIP MORRIS PRODUCTS S.A., Neuchâtel (CH)

(72) Inventors: Gennaro Campitelli, Neuchâtel (CH); Onur Dayioglu, Neuchâtel (CH); Fabiana Spadaro, Lausanne (CH); Gérard Zuber, Boulens (CH)

(73) Assignee: Philip Morris Products S.A., Neuchâtel (CH)

( * ) Notice: Subject to any disclaimer, the term of this patent is extended or adjusted under 35 U.S.C. 154(b) by 1138 days.

(21) Appl. No.: 17/435,131

(22) PCT Filed: Mar. 2, 2020

(86) PCT No.: PCT/IB2020/051760
§ 371 (c)(1),
(2) Date: Aug. 31, 2021

(87) PCT Pub. No.: WO2020/178714
PCT Pub. Date: Sep. 10, 2020

(65) Prior Publication Data
US 2022/0132916 A1     May 5, 2022

(30) Foreign Application Priority Data

Mar. 5, 2019    (EP) .................................... 19160897

(51) Int. Cl.
*A61M 15/00*     (2006.01)
*A24F 13/08*     (2006.01)
*A24F 42/20*     (2020.01)

(52) U.S. Cl.
CPC .............. *A24F 13/08* (2013.01); *A24F 42/20* (2020.01); *A61M 15/003* (2014.02); *A61M 15/0035* (2014.02); *A61M 15/004* (2014.02)

(58) Field of Classification Search
CPC ....... A24F 40/00–95; A61M 11/00–08; A61M 15/00–085
See application file for complete search history.

(56) References Cited

U.S. PATENT DOCUMENTS

| | | | |
|---|---|---|---|
| 3,888,253 A | 6/1975 | Watt et al. | |
| 10,758,686 B2 | 9/2020 | Reevell | |

(Continued)

FOREIGN PATENT DOCUMENTS

| | | | |
|---|---|---|---|
| EP | 02-19-2020 A2 | 2/2020 | |
| GB | 2534208 | 7/2016 | |

(Continued)

OTHER PUBLICATIONS

International Preliminary Report on Patentability for PCT/IB2020/051760, issued Sep. 16, 2021; 8 pages.

(Continued)

*Primary Examiner* — Paige Kathleen Bugg
(74) *Attorney, Agent, or Firm* — Mueting Raasch Group

(57) ABSTRACT

A holder (150) for an inhaler article (110) includes a housing (151) defining an inhaler article cavity (154). A piercing element (160) is fixed to and extends into the inhaler article cavity. A sleeve (180) is disposed within the inhaler article cavity and is configured to retain an inhaler article. The sleeve is movable along the housing longitudinal axis. A spring element (200) is configured to bias the sleeve toward the open proximal end (156) of the housing.

18 Claims, 5 Drawing Sheets

(56)                      References Cited

U.S. PATENT DOCUMENTS

| | | | |
|---|---|---|---|
| 11,045,615 B2 | 6/2021 | Reevell | |
| 2015/0013696 A1* | 1/2015 | Plojoux | A61M 15/06 |
| | | | 131/328 |
| 2016/0331032 A1* | 11/2016 | Malgat | H05B 6/108 |
| 2018/0214645 A1* | 8/2018 | Reevell | A24F 40/53 |
| 2020/0046020 A1* | 2/2020 | Cross | A24F 40/40 |
| 2020/0154765 A1* | 5/2020 | Lee | A24F 40/50 |
| 2020/0170298 A1* | 6/2020 | Lee | A24F 40/46 |

FOREIGN PATENT DOCUMENTS

| | | | |
|---|---|---|---|
| WO | WO 2006/051300 A1 | 5/2006 | |
| WO | 2013/076098 | 5/2013 | |
| WO | 2015/0193498 | 12/2015 | |
| WO | 2017/207586 | 12/2017 | |
| WO | WO 2018/001095 A1 | 1/2018 | |
| WO | WO-2018158207 A1 * | 9/2018 | A61M 11/042 |
| WO | WO 2018/190605 A2 | 10/2018 | |

OTHER PUBLICATIONS

Extended European Search Report for EP 19160897.5, issued by the European Patent Office on Sep. 20, 2019; 9 pgs.
International Search Report and Written Opinion for PCT/IB2020/051760, issued by the European Patent Office on May 25, 2020; 16 pgs.
Indian Office Action for IN Application No. 202117035160 issued by the Indian Patent Office on Jul. 31, 2023; 4 pgs.
Canadian Office Action for CA Application No. 3125961 issued by the Canadian Patent Office on Jun. 17, 2025; 6 pgs.

* cited by examiner

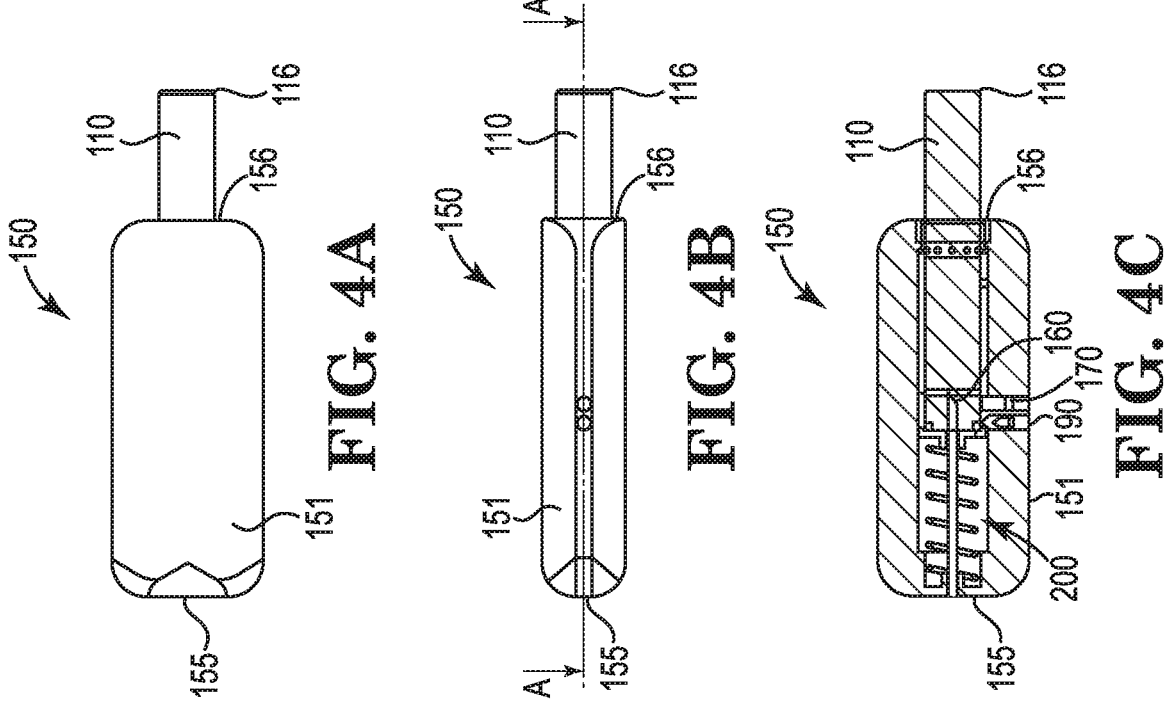

HOLDER FOR INHALER ARTICLE

This application is the § 371 U.S. National Stage of International Application No. PCT/IB2020/051760, filed 2 Mar. 2020, which claims the benefit of European Application No. 19160897.5, filed 5 Mar. 2019.

This disclosure relates to a holder for an inhaler article and inhaler systems that include the holder and an inhaler article. The holder device is configured to activate the inhaler article and hold the inhaler article during consumption.

Dry powder inhalers are not always fully suitable to provide dry powder particles to the lungs at inhalation or air flow rates that are within conventional smoking regime inhalation or air flow rates. Dry powder inhalers may be complex to operate or may involve moving parts. Dry powder inhalers often strive to provide an entire dry powder dose or capsule load in a single breath.

It would be desirable to provide an inhaler system that minimizes moving parts. It would be desirable to provide a holder for an inhaler article that can activate the inhaler article and retain the inhaler article during consumption. It would be desirable to provide a holder for an inhaler article that includes a protected piercing end. It would be desirable to provide an inhaler system that includes a low-profile and reusable holder for an inhaler article that can activate the inhaler article. It would be desirable to provide a nicotine powder inhaler that provides nicotine particles to the lungs at inhalation or air flow rates that are within conventional smoking regime inhalation or air flow rates. It would also be desirable to deliver the nicotine powder with an inhaler article that has a form similar to a conventional cigarette.

This disclosure is directed to a holder for an inhaler article. The holder includes a piercing element that may activate an inhaler article. The activated inhaler article may remain within the holder during consumption. The holder and an inhaler article may form an inhaler system to which this disclosure is also directed.

The holder includes a recessed piercing element and a movable sleeve. An inhaler article is received by the movable sleeve and together they may move toward the piercing element. The piercing element pierces or punctures a hole into a capsule contained within an inhaler article when the inhaler article is pushed into the holder. The sleeve may retain an inhaler article received therein.

A holder for an inhaler device includes, a housing, a piercing element and a sleeve. The housing has a housing outer surface and a housing inner surface. The housing inner surface defines an inhaler article cavity. The housing extends along a housing longitudinal axis from a distal end to an open proximal end a housing length. The housing open proximal end is configured to receive the distal end of an inhaler article into the inhaler article cavity. Preferably, the distal end of the housing is closed. A piercing element is fixed to and extends from the housing inner surface, into the inhaler article cavity along a piercing element longitudinal axis a piercing element length. The piercing element is recessed from the open proximal end a recessed distance. A sleeve is disposed within the inhaler article cavity and configured to retain an inhaler article. The sleeve is movable along the housing longitudinal axis.

A holder for an inhaler device includes, a housing, a piercing element and a sleeve. The housing has a housing outer surface and a housing inner surface. The housing inner surface defines an inhaler article cavity. The housing extends along a housing longitudinal axis from a distal end to an open proximal end a housing length. The housing open proximal end is configured to receive the distal end of an inhaler article into the inhaler article cavity. Preferably, the distal end of the housing is closed. A piercing element is fixed to and extends from the housing inner surface, into the inhaler article cavity along a piercing element longitudinal axis a piercing element length. The piercing element is recessed from the open proximal end a recessed distance. A sleeve is disposed within the inhaler article cavity and configured to retain an inhaler article. The sleeve is movable along the housing longitudinal axis. A spring element may be configured to bias the sleeve toward the open proximal end of the housing.

Advantageously, the holder provides a convenient mechanism to reliably activate a capsule in an inhaler article. The holder may retain the activated inhaler article and a user may grasp the holder and consume particles within the inhaler article.

The holder may include a spring element configured to bias the sleeve toward the open proximal end of the housing, and between a relaxed and compressed position. The spring element may be contained within the inhaler article cavity of the holder and be compressed as the movable sleeve and inhaler article move toward the piercing element. The spring element may be between the sleeve and distal end of the housing and contact the sleeve and distal end of the housing. The spring element may be between the distal end of the sleeve and the distal end of the housing. The spring element may contact the distal end of the sleeve and the distal end of the housing. The spring element may be disposed about the piercing element. The spring element may be co-axial with the piercing element. The spring element may be a conical spring.

Advantageously, the spring element has a compression force that is sufficient to push the inhaler article off of the piercing element while not deforming the inhaler article. The spring element biases the inhaler article away from the piercing element. In use, a user may insert an inhaler article into the inhaler article cavity of the holder. By doing this, the spring may be compressed allowing the inhaler article to move towards the distal end of the inhaler article cavity. Eventually, the piercing element may penetrate a capsule disposed within the inhaler article. Once this happens, the user may release the inhaler article, allowing the spring to bias the inhaler article towards the proximal end of the inhaler article cavity and away from the piercing element. The user may then inhale on the proximal end of the inhaler article.

The sleeve may include an elongated slot extending along a longitudinal length of the sleeve. When the sleeve comprises an elongated slot, the housing may further comprise an alignment pin extending from the inner surface of the inhaler article cavity. The pin may be configured to mate with the elongated slot. This provision of the elongate slot and the corresponding alignment pin may advantageously guide the longitudinal movement of the sleeve in the inhaler article cavity. In particular, the alignment pin may prevent rotation of the sleeve in the inhaler article cavity. This may be particularly advantageous where the holder further comprises a marking element (discussed below). Advantageously, the elongated slot and alignment pin provides for a reliable movement path between a relaxed and compressed position.

The sleeve may define a first air inlet zone comprising at least one air aperture through the sleeve. The first air inlet zone is proximate to a proximal end of the sleeve. The first air inlet zone is configured to allow air to flow from an inside of the sleeve to an airflow channel formed between the sleeve and the housing inner surface. The sleeve may comprise a second air inlet zone comprising at least one air aperture through the sleeve. The second air inlet zone is proximate to a distal end of the sleeve. The second air inlet zone is configured to allow air to flow from the airflow channel to an inside of the sleeve.

The sleeve defines an inner cavity and a portion of the inner cavity may have a reduced internal diameter relative to remaining portions of the inner cavity. Preferably, a portion of the inner cavity may have an internal diameter which is the same as or less than the outer diameter of an inhaler article. This may advantageously allow the inhaler article to be securely retained within the sleeve due to an interference fit.

In some embodiments, the portion of the inner cavity between the first air inlet zone and the second air inlet zone may have a reduced diameter. In these embodiments, the air (inhalation air) is unable to pass from the proximal end of the sleeve to the distal end of the sleeve between the sleeve and the inhalation article. In these embodiments, the provision of a first and second air inlet zone advantageously allows air to enter the open end of the holder and pass to the distal end of an inhaler article while still allowing the article to be securely retained in the sleeve.

The holder may include a marking element that extends into the inhaler article cavity. The marking element is configured to mark the surface of an inhaler article. The marking element may extend orthogonally to the piercing element longitudinal axis. The marking element may be configured to mark the outer surface of an inhaler article in a mechanical manner. For example, the marking element may be configured to scratch, cut, abrade, score, fold, or bend the outer surface of the inhaler article. The marking element may have a sharp end configured to scratch the inhaler outer surface when received within the inhaler article cavity. The marking element may apply a color to the inhaler outer surface when received within the inhaler article cavity. The marking element may be configured to both scratch the inhaler outer surface and apply a color to the inhaler outer surface when received within the inhaler article cavity. The marking element may mark the inhaler outer surface when the piercing element penetrates a capsule disposed within the inhaler article.

The marking element may extend from the inner surface of the housing inner surface, and through the elongated slot of the sleeve to enable the marking element to mark the outer surface of an inhaler article. As discussed above, the provision of an alignment pin may prevent the rotation of the sleeve in the inhaler article cavity. This may advantageously ensure that the marking element is able to extend through the elongated slot at all times. Furthermore, it may also prevent damage to the marking element caused by rotation of the sleeve. Preferably the marking element is axially aligned with the alignment pin. The marking element may be adjacent to the alignment pin. In some embodiments, the alignment pin may also be the marking element.

Advantageously, the marking element marks the inhaler article with an indicator that the inhaler article has been activated. The mark or indication may provide a visual indication that the inhaler article has been activated. The inhaler article may remain in the holder and consumed by a consumer. The holder may be re-utilized on subsequent inhaler articles.

Advantageously, the inhaler system provides an inhaler system that minimizes moving parts. Advantageously, the inhaler system utilizes a separate holder. This may enable the holder to be reusable and the inhaler article to be disposable after a single use. Advantageously, the inhaler system provides nicotine particles to the lungs at inhalation or air flow rates that are within conventional smoking regime inhalation or air flow rates. The inhaler delivers the nicotine powder with an inhaler article that has a form similar to a conventional cigarette. The inhaler system described herein may provide a dry powder to the lungs at inhalation or air flow rates that are within conventional smoking regime inhalation or air flow rates. A consumer may take a plurality of inhalations or "puffs" where each "puff" delivers a fractional amount of dry powder contained within a capsule contained within the capsule cavity. This inhaler article may have a form similar to a conventional cigarette and may mimic the ritual of conventional smoking. This inhaler article may be simple to manufacture and convenient to use by a consumer.

Air flow management through a capsule cavity of the inhaler article may cause a capsule contained therein to rotate during inhalation and consumption. The capsule may contain particles containing nicotine (also referred to as "nicotine powder" or "nicotine particles") and optionally particles comprising flavour (also referred to as "flavour particles"). Rotation of the pierced capsule may suspend and aerosolize the nicotine particles released from the pierced capsule into the inhalation air moving through the inhaler article. The flavour particles may be larger than the nicotine particles and may assist in transporting the nicotine particles into the lungs of the user while the flavour particles preferentially remain in the mouth or buccal cavity of the user. The nicotine particles and optional flavor particles may be delivered with the inhaler article at inhalation or air flow rates that are within conventional smoking regime inhalation or air flow rates.

The term "nicotine" refers to nicotine and nicotine derivatives such as free-base nicotine, nicotine salts and the like.

The term "flavourant" or "flavour" refers to organoleptic compounds, compositions, or materials that alter and are intended to alter the taste or aroma characteristics of nicotine during consumption or inhalation thereof.

The terms "proximal" and "distal" are used to describe the relative positions of components, or portions of components, of the holder, inhaler article, or system. Holders or elements (such as the sleeve) forming the holder, according to the invention have a proximal end which, in use, receives an inhaler article and an opposing distal end which may be a closed end, or have an end closer to the proximal end of the holder. Inhaler articles, according to the invention have a proximal end which, in use, particles exit the inhaler article for delivery to a user and have an opposing distal end. The proximal end of the inhaler article may also be referred to as the mouth end.

The holder for an inhaler device described herein may be combined with an inhaler article containing a capsule for activating the inhaler article by piercing the capsule, providing reliable activation of the capsule (by puncturing the capsule with the piercing element of the holder) within inhaler article, and releasing the particles contained inside the capsule and enabling the article to deliver the particles to a consumer. The holder is separate from the inhaler article, but the consumer may utilize both the inhaler article and the holder while consuming the particles released within the inhaler article. A plurality of these inhaler articles may be combined with a holder to form a system or kit. A single holder may be utilized on 10 or more, or 25 or more, or 50 or more, or 100 or more, inhaler articles to activate (puncture or pierce) a capsule contained within each inhaler article and provide reliable activation and optionally, a visual indication (marking), for each inhaler article of the activation of the inhaler article.

An inhaler system includes an inhaler article and a holder for an inhaler device. The holder is described herein. The inhaler article includes a body having an outer surface. The body extends along an inhaler longitudinal axis from a mouthpiece end to a distal end, a body length, and a capsule disposed within the inhaler article body. The holder includes a piercing element that pierces the capsule when the inhaler article is received in the inhaler article cavity.

A method includes, inserting an inhaler article into the sleeve of the holder for an inhaler device, as described herein. The inhaler article includes a body having an outer surface, the body extending along an inhaler longitudinal axis from a mouthpiece end to a distal end, a body length, and a capsule disposed within the inhaler article body. Then, moving the inhaler article and sleeve toward the piercing element until the piercing element pierces the capsule. Then drawing air into the inhaler article while the inhaler article is disposed within the holder for an inhaler device.

The consumed inhaler article may then be removed from the holder and discarded. Then a fresh inhaler article may be inserted into the holder and the method repeated.

An inhaler article includes a body extending along a longitudinal axis from a mouthpiece end to a distal end. The body has an inhaler length extending between the mouthpiece end and the distal end. The body defines an inhaler outer surface. A capsule cavity is defined within the body and extends along the longitudinal axis. A mouthpiece air channel extends from the capsule cavity to the mouthpiece end. A boundary element is between the capsule cavity and the mouthpiece air channel. The boundary element includes apertures fluidly connecting the capsule cavity with the mouthpiece air channel. The distal end may include an end cap or endpiece element.

A holder for an inhaler device includes, a housing, a piercing element and a sleeve. The housing has a housing outer surface and a housing inner surface. The housing inner surface defines an inhaler article cavity. The housing extends along a housing longitudinal axis from a distal end to an open proximal end a housing length. The housing open proximal end is configured to receive the distal end of an inhaler article into the inhaler article cavity. A piercing element is fixed to and extends from the housing inner surface, into the inhaler article cavity along a piercing element longitudinal axis a piercing element length. The piercing element is recessed from the open proximal end a recessed distance. A sleeve is disposed within the inhaler article cavity and configured to retain an inhaler article. The sleeve is movable along the housing longitudinal axis.

The piercing element is contained within and fixed to the housing inner surface. The piercing element extends along a piercing element longitudinal axis from a fixed distal end to a piercing end a piercing element length. The piercing element is recessed from the open proximal end a recessed distance.

The sleeve may be configured to receive and be disposed about a distal end region of an inhaler article. The sleeve may have a base surface for contacting the distal end of an inhaler article. The base surface may define a distal end of the sleeve and oppose an open proximal end of the sleeve. The sleeve may extend from the distal end to the open proximal end. The sleeve may retain an inhaler article via interference fit.

The sleeve may include an aperture at the distal end of the sleeve and the piercing element may extend thorough the aperture. The distal end of the inhaler article may contact the base surface of the sleeve and urge the sleeve to travel toward the piercing element. The sleeve may be co-axial with the piercing element. The sleeve may align the inhaler article so that the piercing element reliably activates capsule within the inhaler article. The sleeve may also mechanically hold the piercing element and support the piercing element to prevent or mitigate deflection of the piercing element.

The sleeve may include an elongated slot extending along a longitudinal length of the sleeve. When the sleeve comprises an elongated slot, the housing may further comprise an alignment pin extending from the inner surface of the inhaler article cavity. The alignment pin may be configured mate with the elongated slot. The elongated slot may define an elongated opening that extends longitudinally along the sleeve. The elongated slot may extend at least 50% of a length of the sleeve.

The alignment pin engaged with the elongated slot may maintain the linear travel of the sleeve and provide mechanical stability to the sleeve and piercing element. The alignment pin may extend thought a sidewall of the holder. The alignment pin may also be a marking element, as described below.

The sleeve may define a first air inlet zone comprising at least one air aperture through the sleeve. The first air inlet zone may include two or more, three or more, four or more, or from about 1 to about 10 air apertures, or from about 3 to about 9 air apertures. The first air inlet zone is proximate to a proximal end of the sleeve. The first air inlet zone is configured to allow air to flow from an inside of the sleeve to an airflow channel formed between the sleeve and the housing inner surface.

The sleeve may comprise a second air inlet zone comprising at least one air aperture through the sleeve. The second air inlet zone may include two or more, three or more, four or more, or from about 1 to about 10 air apertures, or from about 3 to about 9 air apertures. The second air inlet zone is proximate to a distal end of the sleeve. The second air inlet zone is configured to allow air to flow from the airflow channel to an inside of the sleeve.

The sleeve defines an inner cavity and a portion of the inner cavity may have a reduced internal diameter relative to remaining portions of the inner cavity. Preferably, a portion of the inner cavity may have an internal diameter which is the same as or slightly less than the outer diameter of an inhaler article. This may advantageously allow the inhaler article to be securely retained within the sleeve due to an interference fit.

In some embodiments, the portion of the inner cavity between the first air inlet zone and the second air inlet zone may have a reduced diameter. In these embodiments, the air (inhalation air) is unable to pass from the proximal end of the sleeve to the distal end of the sleeve between the sleeve and the inhalation article. In these embodiments, the provision of a first and second air inlet zone advantageously allows air to enter the open end of the holder and pass to the distal end of an inhaler article while still allowing the article to be securely retained in the sleeve. Thus, the inhaler article may be consumed by a user while the inhaler article is contained within the holder.

The holder may include a retaining ring element fixed to the open proximal end of the housing. The retaining ring element retains the sleeve within the inhaler article cavity. The retaining ring has a thickness sufficient to stop or retain the movement of the sleeve within the inhaler article cavity of the holder.

The holder may include a spring element configured to bias the sleeve between a relaxed and compressed position towards the open proximal end of the housing. The spring element may be contained within the inhaler article cavity of the holder and be compressed as the movable sleeve and inhaler article move toward the piercing element. The spring element may be between the sleeve and distal end of the housing and contacts the sleeve and distal end of the housing. The spring element may be disposed about the piercing element. The spring element may be co-axial with the piercing element. The spring element may be a conical spring.

The spring element may be fixed to the distal end of the holder. The spring element may be fixed to the distal end of the sleeve. The spring element may be fixed to both the distal end of the holder and the distal end of the sleeve. The spring element may be a conical spring. The conical spring advantageously may provide a low-profile design so that it may provide a more flexible design and smaller overall compression thickness. The provision of a conical spring may also advantageously reduce the likelihood that the spring will buckle when compressed compared to a cylindrical spring.

The spring element has a compression force that is sufficient to push the inhaler article off of the piercing element while not deforming the inhaler article. The spring element may have a compression force of about 10 N or less, or about 8 N or less, or about 6 N or less, or in a range from about 1 to about 10 N, or in a range from about 2 N to about 8 N, or in a range from about 2 N to about 6 N. The inhaler article may deform at compression forces about 10 N, or above about 8 N.

The spring element biases the inhaler article off of and away from the piercing element once the piercing element activates the inhaler article. The spring element may be disposed about the piercing element. The spring element may be coaxial with the piercing element. The piercing element may extend beyond the spring element when the spring element is in a relaxed position. The piercing element may extend beyond the spring element when the spring element is in a compressed position. The piercing element may extend beyond the spring element when the spring element is in both the relaxed position and the compressed position. The piercing element may extend beyond the spring element when the sleeve compresses the spring element.

The sleeve may include an elongated slot extending along a longitudinal length of the sleeve. When the sleeve comprises an elongated slot, the housing may further comprise an alignment pin extending from the inner surface of the inhaler article cavity. The alignment pin may be configured to mate with the elongated slot. The sleeve may include two or more air inlet apertures. Advantageously, the elongated slot and alignment pin provides for a reliable movement path between a relaxed and compressed position.

The holder may include a marking element that extends into the inhaler article cavity. The marking element is configured to mark the surface of an inhaler article. The marking element may extend orthogonally to the piercing element longitudinal axis. The marking element may be configured to mark the outer surface of an inhaler article in a mechanical manner. For example, the marking element may be configured to scratch, cut, abrade, score, fold, or bend the outer surface of the inhaler article. The marking element may have a sharp end configured to scratch the inhaler outer surface when received within the inhaler article cavity. The marking element may apply a color to the inhaler outer surface when received within the inhaler article cavity.

The marking element may mark the inhaler outer surface when the piercing element penetrates a capsule disposed within the inhaler article. Thus, indicating that the inhaler article has been activated and may be consumed by a user. This may also advantageously prevent a user trying to reuse an inhaler article which has already been previously activated.

The marking element may extend orthogonally to the piercing element longitudinal axis. The marking element may be formed of a rigid material configured to provide a visual indication that the marking element has contacted the inhaler outer surface. The marking element may be fixed to the holder housing. The marking element may form the alignment pin, as described above.

The marking element may extend though at least a portion of a thickness of the holder. The marking element extends through the sleeve. The marking element may extend into the inhaler article cavity and into the sleeve. The marking element may extend beyond the at least the sleeve a marking distance so that the marking element contacts the inhaler outer surface when the inhaler article is received within the inhaler article cavity. The marking element may be aligned with and mate with the elongated slot of the sleeve.

The marking element may define a pin shape having a length greater than its diameter. The marking element may be threaded and resemble a screw. The distance the marking element extends into the inhaler article receptacle may be varied by the consumer. For example, the marking element may be rotated to change the distance the marking element extends into the inhaler article receptacle. This may advantageously allow the marking element to be used with different inhaler articles having different diameters. The marking element may have a length that is greater than the thickness of the housing and sleeve that it extends through.

The marking element may have a sharp end configured to scratch the inhaler outer surface when received within the inhaler article cavity. This marking element may be formed from a metal. The marking element may be configured to mark the outer surface of an inhaler article in a mechanical manner. For example, the marking element may be configured to scratch, cut, abrade, score, fold, or bend the outer surface of the inhaler article. The marking element may have a sharp end configured to scratch the inhaler outer surface when received within the inhaler article cavity. The marking element may mark the inhaler outer surface when the piercing element penetrates a capsule disposed within the inhaler article.

This sharp marking element may form a scratch that is visually apparent to the consumer. The visual scratch on the inhaler outer surface may indicate that the piercing element penetrated a capsule received within the inhaler article, thus indicating that the inhaler article has been activated and may be consumed by a user.

The marking element may apply a color to the inhaler outer surface when received within the inhaler article cavity. The marking element may include at least one of, a graphite core, chalk, and ink to provide a visual color mark that is apparent to the consumer. The visual color mark on the inhaler outer surface may indicate that the piercing element penetrated a capsule received within the inhaler article, thus indicating that the inhaler article has been activated and may be consumed by a user.

Recessing the piercing element into the housing protects the piercing element from coming into contact with surfaces not intended to be received within the piercing element. Recessing the piercing element into the housing may also protect the piercing element from being damaged or modified by surfaces not intended to be received within the piercing element.

The piercing element may be recessed from the open proximal end by any suitable recessed distance. For example, the piercing element may be recessed from the open proximal end a recessed distance of at least about 10%, at least about 20%, at least about 25%, or at least about 30%, or at least about 35%, or at least about 40%, of the housing length. The piercing element may be recessed from the open proximal end a recessed distance of in a range from about 5% to about 50%, or from about 10% to about 40%, or from about 15% to about 40%, or about 20% to about 40%, of the housing length.

The piercing element length may be any suitable length relative to the housing length. For example, the piercing element length may be about 25% to about 60%, or about 30% to about 50%, of the housing length. A distal end of the piercing element may be fixed to the distal end adjacent to or at the distal end of the housing. The piercing element entire length may be coextensive within the housing length.

The housing inner surface has an open proximal end diameter and a distal end diameter. The distal end diameter may be less than the open proximal end diameter. The housing inner surface diameter may taper down from the open proximal end diameter to the distal end diameter. The housing inner surface diameter may taper down by any suitable amount. For example, the housing inner surface diameter may taper down in a range from about 3% to about 13%, or about 5% to about 10% of the housing inner diameter at the proximal end.

The piercing element is formed of a rigid material. The rigid material is sufficiently rigid to pierce, puncture or activate a capsule contained within the inhaler article. The piercing element may be formed of a metal. The piercing element may be formed of stainless steel, such as 316 stainless steel, for example. The piercing element may be formed of a polymeric material. The piercing element may be formed of a fibre-reinforced polymeric material.

Polymeric materials useful for forming the piercing element include polycarbonate, polypropylene, polyethylene, nylon, acrylonitrile butadiene styrene, styrene acrylonitrile, polyacrylate, polystyrene, PBT polyester, PET polyester, polyoxymethylene, polysulfone, polyethersulfone, polyethereetherketone, or liquid crystal polymer, for example. Polycarbonate or liquid crystal polymer are preferred materials for forming the piercing element.

The polymeric material may be fibre-reinforced and include a plurality of fibres forming a fibre dispersion throughout the piercing element. Fibres forming this fibre dispersion may have an average length of less than about 1 mm, or in a range from about 0.1 mm to about 1 mm, and an average diameter of less than 50 micrometers. The fibres forming the fibre dispersion may be formed of glass, carbon, basalt, graphite, DuPont Kevlar brand aramid fibres, ceramics, natural fibres, polymeric fibres, and metal, for example. Preferably fibres forming the fibre dispersion are composed of glass fibres. The fibre dispersion when present in the polymeric material forming the piercing element may range from about 5% to about 60% by weight, or from about 10% to about 50% by weight, or from about 20% to about 45% by weight, or from about 30% to about 40% by weight. Fibre-reinforced polycarbonate or fibre-reinforced liquid crystal polymer are preferred materials for forming the piercing element.

The housing may be formed of any rigid material. The housing may be formed of a polymeric material. Polymeric materials useful for forming the housing include polycarbonate, polypropylene, polyethylene, nylon, acrylonitrile butadiene styrene, styrene acrylonitrile, polyacrylate, polystyrene, PBT polyester, PET polyester, polyoxymethylene, polysulfone, polyethersulfone, polyethereetherketone, or liquid crystal polymer, for example. Polyproplyene, polyethylene or co-polymers thereof are preferred materials for forming the housing.

The polymeric material forming the housing may be a different type of polymeric material than the polymeric material forming the piercing element. In one example, the polymeric material forming the housing may be polyproplyene, polyethylene or co-polymers thereof, and the polymeric material forming the piercing element may be fibre-reinforced polycarbonate, liquid crystal polymer, or fibre-reinforced liquid crystal polymer.

The piercing element may define two or more diameters. The piercing element may have a first diameter adjacent the piercing end and a second diameter being greater than the first diameter adjacent to the fixed distal end. The piercing element may have a first length segment adjacent the piercing end and a second length segment adjacent to the fixed distal end. The first length segment may have a substantially constant or uniform diameter. The second length segment may have a substantially constant or uniform diameter, or the second length segment may have a tapering diameter decreasing from the fixed distal end to the first length segment.

The inhaler article may be received into the holder such that the inhaler article outer surface and the holder housing outer surface are concentric. The piercing element longitudinal axis may be coaxial with the housing longitudinal axis, and the inhaler longitudinal axis, when the inhaler article is received within the holder. At least about 50%, or at least about 75% of the housing length may be coextensive with the inhaler length, when the inhaler article is received within the holder.

The holder may be formed by insertion moulding techniques. The piercing element may first be formed by moulding, for example, and then the housing may be moulded around the piercing element bonding to the piercing element. The piercing element may be a metal piercing element, the housing may be moulded around the metal piercing element fixing the metal piercing element to the housing. A metal piercing element may include protrusions or recesses at the distal end of the piercing element to increase surface area of the distal end of the piercing element and improve fixation within the housing moulded material.

An inhaler article air channel may extend through the end cap or endpiece element of the inhaler article to provide airflow through the inhaler article. The air channel supplying airflow to the capsule cavity may be configured to induce a swirling air flow pattern within the capsule cavity of the inhaler body. The air channel configuration may induce rotational air flow or swirling air flow as the air flows through the air channel and through the capsule cavity. Air flow through the inhaler device may enter the inhaler device at the distal end of the inhaler device and moves along the longitudinal axis of the inhaler device to the mouthpiece end. Air flow through the inhaler device may enter the inhaler device along the inhaler body upstream or along the capsule cavity and move along the longitudinal axis of the inhaler device to the mouthpiece end.

The inhaler article end cap or endpiece element may include a linear piercing channel extending through the length of the end cap or end piece element. The linear piercing channel may extend along a central axis of the end cap or end piece element. The linear piercing channel may be co-axial with the longitudinal axis of the inhaler body. The linear piercing channel may be sized to allow a piercing element to pass through the linear piercing channel. The end cap or endpiece element may define a resealable element disposed along or within the linear piercing channel. The resealable element may seal the linear piercing channel. The resealable element may form an airtight seal or barrier along the linear piercing channel, when a piercing element is not within the resealable element. The linear piercing channel may be formed of a pierce-able material. A piercing element may pass through the resealable element and puncture the capsule within the capsule cavity. The resealable element may reseal once the piercing element is retracted or removed from the resealable element. Resealable elements or membranes may include a septum or septum-like element. Resealable elements or membranes may be formed of elastic material such as rubber, silicone, metal foil co-laminated with a polymer, or latex and the like, or cellulose acetate tow, such as high-density cellulose acetate tow.

The inhaler body may resemble a smoking article or cigarette in size and shape. The inhaler body may have an elongated body extending along the longitudinal axis of the inhaler article. The inhaler body may have a substantially uniform outer diameter along the length of the elongated body. The inhaler body may have a circular cross-section that may be uniform along the length of the elongated body. The inhaler body may have an outer diameter in a range from about 6 mm to about 10 mm, or from about 7 mm to about 10 mm, or about 7 mm to about 9 mm, or about 7 mm to about 8 mm or about 8 mm. The inhaler body may have a length (along the longitudinal axis) in a range from about 40 mm to about 90 mm, or from about 50 mm to about 80 mm, or about 50 mm to about 70 mm, or 55 mm.

The capsule cavity may define a cylindrical space configured to contain a capsule (that may have an obround shape or a circular cross-section, for example). The capsule cavity may have a substantially uniform or uniform diameter along the length of the capsule cavity. The capsule cavity may have a fixed cavity length. The capsule cavity has a cavity inner diameter, orthogonal to the longitudinal axis, and the capsule has a capsule outer diameter. The capsule cavity may be sized to contain an obround capsule. The capsule cavity may have a substantially cylindrical or cylindrical cross-section along the length of the capsule cavity. The capsule cavity may have a uniform inner diameter. The capsule may have an outer diameter that is about 85% to about 95% of the inner diameter of the capsule cavity. The configuration of the capsule cavity relative to the capsule may promote limited movement of the capsule during activation or piercing of the capsule.

The configuration of the capsule cavity relative to the capsule may promote the capsule to rotate with stability within the capsule cavity. The longitudinal axis of the capsule may rotate with stability co-axially with the longitudinal axis of the inhaler body during inhalation.

Stable rotation refers to the longitudinal axis of the inhaler body being substantially parallel or co-axial with the axis of rotation of the capsule. Stable rotation may refer to the absence of procession of the rotating capsule. Preferably the longitudinal axis of the inhaler body may be substantially coextensive with the axis of rotation of the capsule. Stable rotation of the capsule may provide a uniform entrainment of a portion of nicotine particles from the capsule over two or more, or five or more, or ten or more "puffs" or inhalations by a consumer.

The capsule may be sealed within the inhaler article prior to consumption. The inhaler article may be contained within a sealed or airtight container or bag. The inhaler article may include one or more peelable or removable seal layers to cover the one or more air inlet channels or the air outlet or mouthpiece of the inhaler article.

The capsule may rotate about its longitudinal or central axis when air flows through the inhaler article. The capsule may be formed of an airtight material that may be pierced or punctured by a piercing element that may be separate or combined with the inhaler. The capsule may be formed of a metallic or polymeric material that serves to keep contaminates out of the capsule but may be pierced or punctured by a piercing element prior to consumption of the nicotine particles within the capsule. The capsule may be formed of a polymer material. The polymer material may be hydroxy-propylmethylcellulose (HPMC). The capsule may be a size 1 to size 4 capsule, or a size 3 capsule.

The separate holder, described, forms a single aperture through the capsule received in the capsule cavity. The holder piercing element may pass through the resealable element sealing the piercing channel on the end cap.

The capsule contains nicotine particles comprising nicotine (also referred to as "nicotine powder" or "nicotine particles") and optionally particles comprising flavour (also referred to as "flavour particles). The capsule may contain a predetermined amount of nicotine particles and optional flavour particles. The capsule may contain enough nicotine particles to provide at least 2 inhalations or "puffs", or at least about 5 inhalations or "puffs", or at least about 10 inhalations or "puffs". The capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The capsule may hold or contain at least about 5 mg of a dry powder (also referred to as a powder system) or at least about 10 mg of a dry powder. The capsule may hold or contain less than about 900 mg of a dry powder, or less than about 300 mg of a dry powder, or less than about 150 mg of a dry powder. The capsule may hold or contain from about 5 mg to about 300 mg of a dry powder, or from about 10 mg to about 200 mg of a dry powder.

The dry powder or powder system may have at least about 40%, or at least about 60%, or at least about 80%, by weight of the powder system comprised in nicotine particles having a particle size of about 5 micrometers or less, or in a range from about 1 micrometer to about 5 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

The dry powder may have a mean diameter of about 60 micrometres or less, or in a range from about 1 micrometres to about 40 micrometres, or in a range from about 1.5 micrometres to about 25 micrometres. The mean diameter refers to the mean diameter per mass and is preferably measured by laser diffraction, laser diffusion or an electronic microscope.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine mono-pyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles. Similarly, adhesion forces to particles comprising flavour may also be reduced thus agglomeration of nicotine particles with flavour particles is also reduced. The powder system described herein thus may be a free flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include a population of flavour particles. The flavour particles may have any useful size distribution for inhalation delivery selectively into the mouth or buccal cavity of a user.

The powder system may have at least about 40%, or at least about 60%, or at least about 80%, by weight of the population of flavour particles of the powder system comprised in particles having a particle size of about 20 micrometres or greater. The powder system may have at least about 40% or at least about 60%, or at least about 80%, by weight of the population of flavour particles of the powder system comprised in particles having a particle size of about 50 micrometres or greater. The powder system may have at least about 40% or at least about 60%, or at least about 80%, by weight of the population of flavour particles of the powder system comprised in particles having a particle size in a range from about 50 micrometer to about 150 micrometres.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus, agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

Conventional formulations for dry powder inhalation contain carrier particles that serve to increase the fluidization of the active particles since the active particles may be too small to be influenced by simple airflow though the inhaler. The powder system may comprise carrier particles. These carrier particles may be a saccharide such as lactose or mannitol that may have a particle size greater than about 50 micrometres. The carrier particles may be utilized to improve dose uniformity by acting as a diluent or bulking agent in a formulation.

The powder system utilized with the nicotine powder delivery system described herein may be carrier-free or substantially free of a saccharide such as lactose or mannitol. Being carrier-free or substantially free of a saccharide such as lactose or mannitol may allow the nicotine and to be inhaled and delivered to the user's lungs at inhalation or airflow rates that are similar to typical smoking regime inhalation or airflow rates.

The nicotine particles and a flavour may be combined in a single capsule. As described above, the nicotine particles and a flavour may each have reduced adhesion forces that result in a stable particle formulation where the particle size of each component does not substantially change when combined. Alternatively, the powder system includes nicotine particles contained within a single capsule and the flavour particles contained within a second capsule.

The nicotine particles and flavour particles may be combined in any useful relative amount so that the flavour particles are detected by the user when consumed with the nicotine particles. Preferably the nicotine particles and a flavour particles form at least about 90% wt or at least about 95% wt or at least about 99% wt or 100% wt of the total weight of the powder system.

The inhaler and inhaler system may be less complex and have a simplified airflow path as compared to conventional dry powder inhalers. Advantageously, rotation of the capsule within the inhaler body aerosolizes the nicotine particles or powder system and may assist in maintaining a free-flowing powder. Thus, the inhaler article may not require the elevated inhalation rates typically utilized by conventional inhalers to deliver the nicotine particles described above deep into the lungs.

The inhaler article may use a flow rate of less than about 5 L/min or less than about 3 L/min or less than about 2 L/min or about 1.6 L/min. Preferably, the flow rate may be in a range from about 1 L/min to about 3 L/min or from about 1.5 L/min to about 2.5 L/min. Preferably, the inhalation rate or flow rate may be similar to that of Health Canada smoking regime, that is, about 1.6 L/min.

The inhaler system may be used by a consumer like smoking a conventional cigarette or vaping an electronic cigarette. Such smoking or vaping may be characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer may determine the amount of nicotine to be inhaled. During the second step, the consumer may determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIG. 4A is a side elevation schematic diagram of an illustrative flat holder.

FIG. 4B is a top elevation schematic diagram of the illustrative flat holder of FIG. 4A.

FIG. 4C is a cross-sectional schematic diagram of the illustrative flat holder of FIG. 4B taken along line A-A.

Figure 1:
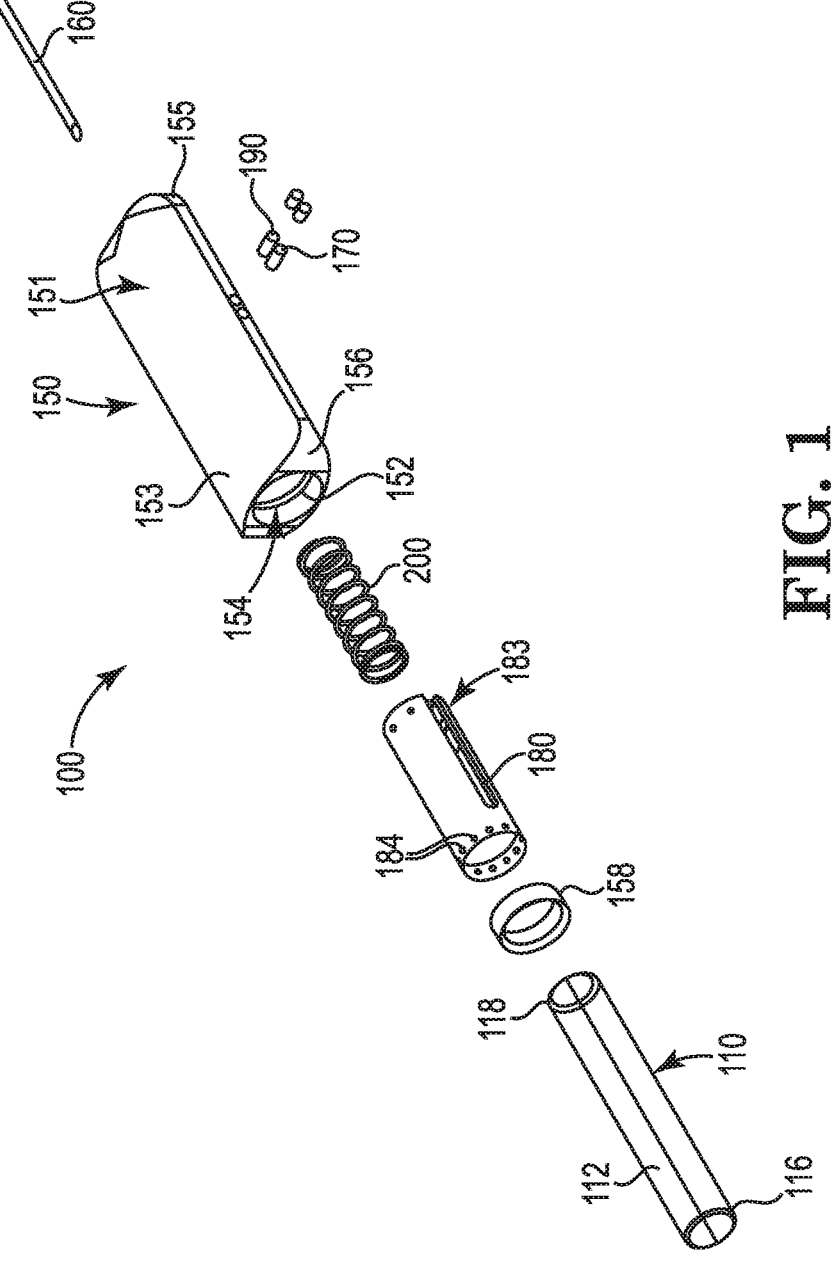
FIG. 1 is an exploded perspective view of an illustrative inhaler system.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

An inhaler system 100 includes an inhaler article 110 and a holder 150. The inhaler article 110 comprises a body 112 defining an inhaler outer surface. The body 112 extends along an inhaler longitudinal axis from mouthpiece, or proximal end 116 to a distal end 118 a body length.

A holder 150 for an inhaler device 110 includes, a housing 151, a piercing element 160 and a sleeve 180. The housing 151 has a housing outer surface 153 and a housing inner surface 152. The housing inner surface 152 defines an inhaler article cavity 154. The housing 151 extends along a housing longitudinal axis from a distal end 155 to an open proximal end 156 a housing length. The housing open proximal end 156 is configured to receive the distal end 118 of an inhaler article 110 into the inhaler article cavity 154. A piercing element 160 is fixed to and extends from the housing inner surface 152, into the inhaler article cavity 154 along a piercing element longitudinal axis a piercing element length. The piercing element 160 is recessed from the open proximal end 156 a recessed distance. A sleeve 180 is disposed within the inhaler article cavity 154 and configured to retain an inhaler article 110. The sleeve 180 is movable along the housing longitudinal axis.

Figure 2:
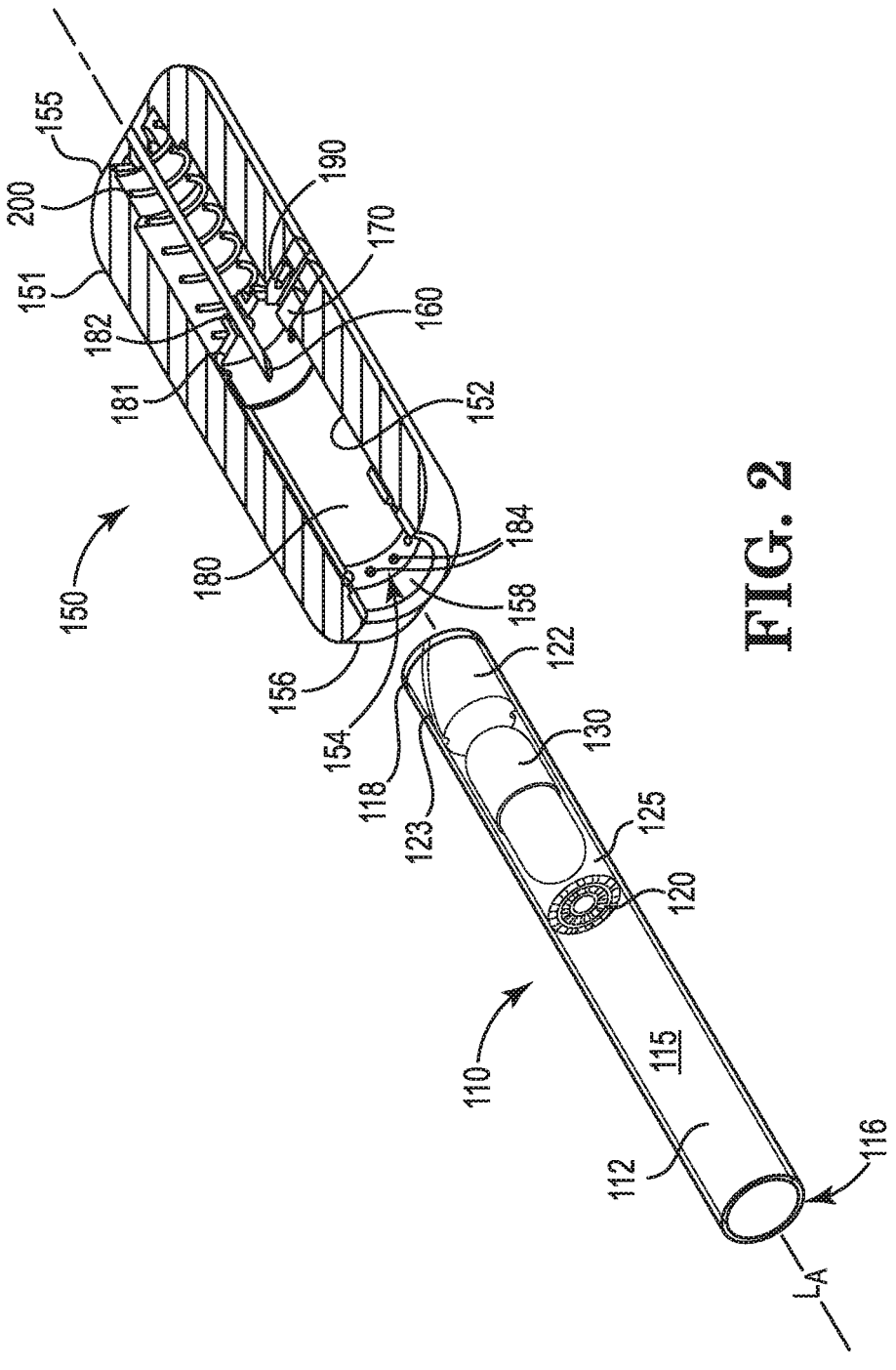
FIG. 2 is a cross-sectional schematic diagram of an illustrative holder.
Figures 3A, 3B, 3C:
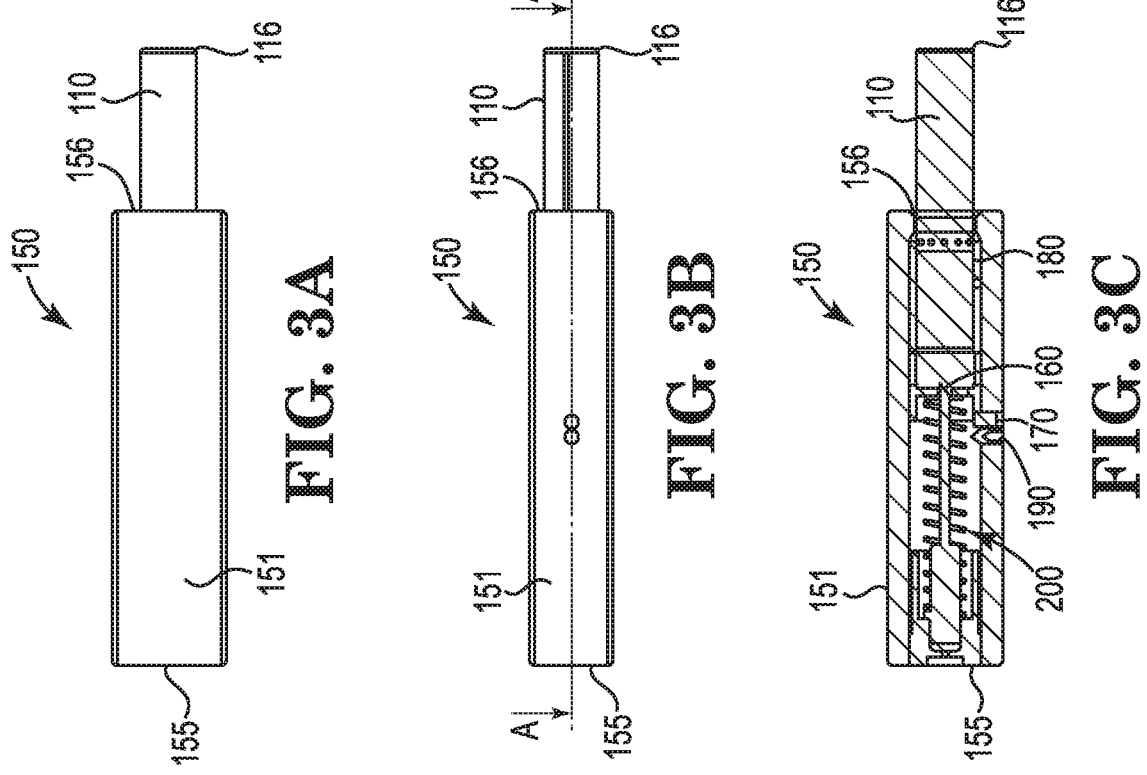
FIG. 3A is a side elevation schematic diagram of an illustrative rectangular holder.
FIG. 3B is a top elevation schematic diagram of the illustrative rectangular holder of FIG. 3A.
FIG. 3C is a cross-sectional schematic diagram of the illustrative rectangular holder of FIG. 3B taken along line A-A.

FIG. 1 illustrates an exploded perspective view an exemplary inhaler system 100. FIG. 2 is a cross-sectional schematic diagram of an illustrative holder 150. FIG. 3A is a side elevation schematic diagram of an illustrative rectangular holder 150. FIG. 3B is a top elevation schematic diagram of the illustrative rectangular holder 150 of FIG. 3A. FIG. 3C is a cross-sectional schematic diagram of the illustrative rectangular holder 150 of FIG. 3B taken along line A-A. FIG. 4A is a side elevation schematic diagram of an illustrative flat holder 150. FIG. 4B is a top elevation schematic diagram of the illustrative flat holder 150 of FIG. 4A. FIG. 4C is a cross-sectional schematic diagram of the illustrative flat holder 150 of FIG. 4B taken along line A-A.

The inhaler system 100 includes an inhaler article 110 and a separate holder 150. The inhaler article 110 may be received within the holder 150 to activate or pierce a capsule 130 disposed within the inhaler article 110. The inhaler article 110 may remain in the holder 150 during use by the consumer.

The inhaler article 110 includes a body 112 extending along a longitudinal axis $L_A$ from a mouthpiece end 116 to a distal end 118 and a capsule cavity 125 defined within the body 112. The body 112 may have a uniform diameter of about 7.5 mm and a length of about 55 mm. The body 112 may have a uniform diameter inner diameter of about 6.5 mm. The body 112 may have a uniform thickness about 1 mm. A mouthpiece air channel 115 extends from the capsule cavity 125 to the mouthpiece end 116. An end cap or end element 122 is disposed within the distal end 118 and extends to the capsule cavity 125. The end cap or end element 122 includes an air channel 123 extending along the end cap or end element 122. The air channel 123 creates a swirling airflow through the capsule cavity 125. The end cap or end element 122 and a boundary element 120 bound the capsule cavity 125. A capsule 130 is disposed within the capsule cavity 125. The capsule 130 contains particles comprising nicotine. The end cap or end element 122 and the boundary element 120 cooperate to contain the capsule 130 longitudinally within the capsule cavity 125. The capsule 130 axis of rotation may be coextensive with the longitudinal axis $L_A$.

The inhaler article end cap or end element 122 may include a linear piercing channel extending through the length of the end cap or end element 122. The linear piercing channel may be co-axial with the longitudinal axis $L_A$ of the inhaler body 112. The linear piercing channel may be sized to allow a piercing element 160 to pass through the linear piercing channel. The end cap or end element 122 may define a resealable element disposed along or within the linear piercing channel. Resealable elements or membranes may include a septum or septum-like element. Resealable elements or membranes may be formed of elastic material such as rubber, silicone, metal foil co-laminated with a polymer, or latex and the like, or cellulose acetate tow, such as high-density cellulose acetate tow.

The sleeve 180 may have a base surface 181 for contacting the distal end 118 of an inhaler article 110. The base surface 180 may define a distal end of the sleeve 180 and oppose an open proximal end of the sleeve 180. The sleeve 180 may extend from the distal end to the open proximal end.

The sleeve 180 may include an aperture 182 and the piercing element 160 may extend thorough the aperture 182. The distal end 118 of the inhaler article 110 may contact the base surface 181 of the sleeve 180 and urge the sleeve to travel toward the piercing element 160.

The sleeve 180 may include an elongated slot 183 extending along a longitudinal length of the sleeve 180 and an alignment pin 170 extends from the inner surface 152 of the inhaler article cavity 154 and the alignment pin 170 configured to mate with the elongated slot 183. The elongated slot 183 may define an elongated opening that extends longitudinally along the sleeve 180.

Figure 5:
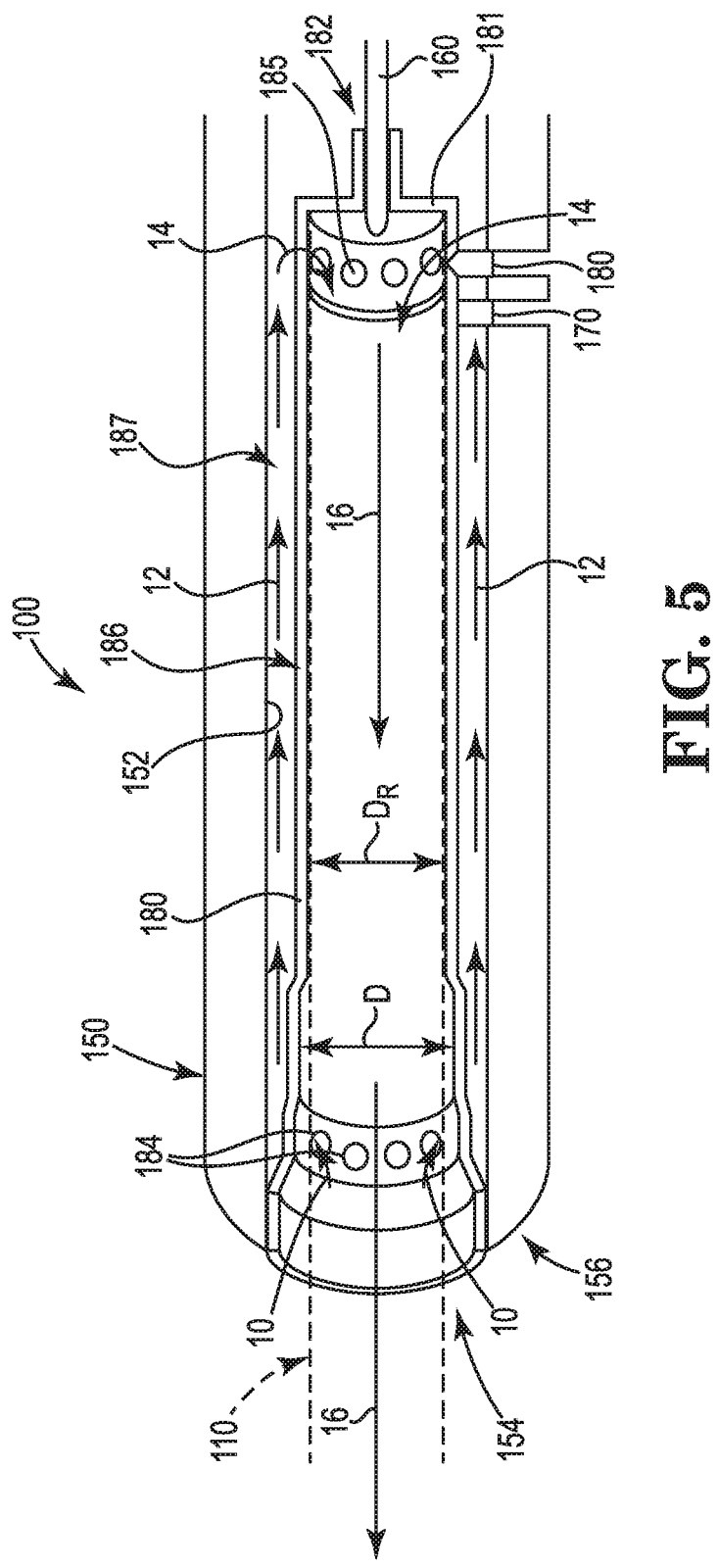
FIG. 5 is a cross-sectional schematic diagram illustrating air flow through an inhaler article and system.

The sleeve 180 may include two or more air inlet apertures 184. The air inlet apertures 184 may extend through the sidewall of the sleeve 180 to allow inlet air to pass through the sleeve 180, as illustrated in FIG. 5 and described below. Thus, a consumer may draw air though the inhaler article 110 while the inhaler article 110 is seated onto the holder 150. Inlet air may flow from the open proximal end 156 of the housing 151 through the two or more air inlet apertures 184 and along an air channel formed between the sleeve 180 and the inner surface 152 of the inhaler article 110 to the air inlets of the inhaler article 123.

The holder 150 may include a retaining ring element 158 fixed to the open proximal end 156 of the housing 151. The retaining ring element 158 retains the sleeve 180 within the inhaler article cavity 154.

The holder 150 may include a spring element 200 configured to bias the sleeve 180 between a relaxed and compressed position. The spring element 200 may be contained within the inhaler article cavity 154 of the holder 150 and be compressed as the movable sleeve 180 and inhaler article 110 move toward the piercing element 160. The spring element 200 may be fixed to the distal end 155 of the holder 150 or fixed to the distal end of the sleeve 180, or fixed to both.

The spring element 200 biases the inhaler article 110 off of and away from the piercing element 160 once the piercing element 160 activates the inhaler article 110 by puncturing the capsule 130.

The housing 150 may have an overall longitudinal length in a range from about 40 mm to about 60 mm. The sleeve 180 may have an overall longitudinal length in a range from about 15 mm to about 30 mm. The spring element 200 may have an overall longitudinal length in a range from about 15 mm to about 30 mm. The sleeve 180 may travel or be movable an overall longitudinal distance in a range from about 15 mm to about 30 mm. The spring 200 may compress an overall longitudinal distance in a range from about 15 mm to about 30 mm.

In one embodiment, the inhaler article 110 has a longitudinal length of about 45 mm, and the housing 150 has a longitudinal length of about 50 mm to about 55 mm. Once received in the holder 150 (and the sleeve 180 and spring element 200 in the relaxed position), the inhaler article 110 has about 50% of its longitudinal length received within the holder 150 and about 50% of its longitudinal length extending from the holder 150. In this embodiment, A consumer may urge the inhaler article 110 onto the piercing element, compressing the spring element 200, puncturing the capsule 130 to activate the capsule 130. In the compressed position, less than about 10% of the inhaler article 110 longitudinal length extends from the holder 150 or about 1 mm to about 5 mm of the inhaler article 110 longitudinal length extends from the holder 150. The linear or longitudinal distance between the relaxed and compressed position may be from about 15 mm to about 25 mm, or about 20 mm.

The holder may include a marking element 190. The marking element 190 places a mark on the inhaler outer surface 112 to indicate that the capsule 130 has been activated or pierced. Then the inhaler article 110 may be maintained within the holder 150 and consumed by the user and the consumed inhaler article 110 may be replaced and user may then repeat this method with the holder 150 and further a non-activated inhaler article 110.

FIG. 5 is a cross-sectional schematic diagram illustrating air flow though ah inhaler system 100. An inhaler article 110 is shown in broken lines and received within the sleeve 180 of the holder 150.

The sleeve 180 may define a first air inlet zone comprising at least one air aperture 184 through the sleeve 180. The first air inlet zone is proximate to a proximal end of the sleeve 180. The first air inlet zone is configured to allow air 10 to flow from inside of the sleeve 180 to an airflow channel 187 formed between the sleeve 180 and the housing inner surface 152. Airflow 12 moves from the first air inlet zone to the second air inlet zone.

The sleeve 180 may comprise a second air inlet zone comprising at least one air aperture 185 through the sleeve 180. The second air inlet zone is proximate to a distal end of the sleeve 180. The second air inlet zone is configured to allow air 14 to flow from the airflow channel 187 to inside of the sleeve 180.

The sleeve 180 defines an inner cavity 186 and a portion of the inner cavity 186 may have a reduced internal diameter $D_R$ relative to remaining portions of the inner cavity D. Preferably, a portion of the inner cavity 186 may have an internal diameter $D_R$ which is the same as or slightly less than the outer diameter of an inhaler article 110. This may advantageously allow the inhaler article 110 to be securely retained within the sleeve 180 due to an interference fit.

The portion of the inner cavity 186 between the first air inlet zone and the second air inlet zone may have a reduced diameter $D_R$ which is the same as or slightly less than the outer diameter of an inhaler article 110. In these embodiments, the air (inhalation air) is unable to pass from the proximal end of the sleeve to the distal end of the sleeve 180 between the sleeve 180 and the inhalation article 110. In these embodiments, the provision of a first and second air inlet zone 184, 185 advantageously allows air 10 to enter the open end 154 of the holder 150 and pass to the distal end of an inhaler article while still allowing the inhaler article 110 to be securely retained in the sleeve 180.

Inhalation air 10 enters the open end 154 of the holder 150 and passes through the sleeve 180 at the first air inlet zone 184 forming channel air 12 flowing along airflow channel 187 to the second air inlet zone 185. Air 14 flows into the inner cavity 186 via the second air inlet zone 185 and into the inhaler article 110. Air 16 flows through the inhaler article 110 to the consumer.

The invention claimed is:

1. An inhaler system comprising:
an inhaler article comprising a body having an outer surface, the body extending along an inhaler article longitudinal axis from a mouthpiece end to a distal end, a body length, and a capsule disposed within the body; and
a holder for the inhaler article, the holder comprising:
a housing, having a housing outer surface and a housing inner surface, the housing inner surface defining an inhaler article cavity, the housing extending along a housing longitudinal axis from a distal end to an open proximal end along a housing length, the open proximal end configured to receive the distal end of the inhaler article into the inhaler article cavity;
a piercing element is configured to penetrate the capsule, wherein the piercing element fixed to and extending from the housing inner surface, into the inhaler article cavity along a piercing element longitudinal axis extending along a piercing element length, the piercing element being recessed from the open proximal end a recessed distance;
a sleeve disposed within the inhaler article cavity and configured to retain the inhaler article, the sleeve being movable along the housing longitudinal axis; and
a spring element configured to bias the sleeve toward the open proximal end of the housing;
wherein the piercing element pierces the capsule when the inhaler article is received in the inhaler article cavity.

2. The inhaler system according to claim 1, wherein the sleeve extends from a sleeve open proximal end to a sleeve distal end and a base surface located at the sleeve distal end, and wherein the piercing element extends into the sleeve through the base surface.

3. The inhaler system according to claim 2, wherein the distal end of the inhaler article contacts the base surface of the sleeve.

4. The inhaler system according to claim 1, wherein inhalation air enters the open proximal end and then enters the distal end of the inhaler article.

5. The inhaler system according to claim 3, wherein inhalation air enters the open proximal end and then enters the distal end of the inhaler article.

6. The inhaler system according to claim 1, wherein the sleeve retains the inhaler article via interference fit.

7. The inhaler system according to claim 1, wherein the spring element is disposed within the inhaler article cavity between the sleeve and the distal end of the housing and contacts the sleeve and the distal end of the housing.

8. The inhaler system according to claim 1, wherein the spring element is disposed about the piercing element.

9. The inhaler system according to claim 1, wherein the spring element is a conical spring.

10. The inhaler system according to claim 1, wherein the piercing element extends beyond the spring element when the sleeve compresses the spring element.

11. The inhaler system according to claim 1, wherein the sleeve comprises an elongated slot extending along a longitudinal length of the sleeve and the housing further comprises an alignment pin extending from the housing inner surface into the inhaler article cavity, the pin being configured to mate with the elongated slot.

12. The inhaler system according to claim 1, wherein the sleeve defines a first air inlet zone comprising at least one air aperture through the sleeve, the first air inlet zone proximate to a proximal end of the sleeve, the first air inlet zone configured to allow air to flow from an inside of the sleeve to an airflow channel formed between the sleeve and the housing inner surface, and the sleeve comprises a second air inlet zone comprising at least one air aperture through the sleeve, the second air inlet zone proximate to a distal end of the sleeve, the second air inlet zone configured to allow air to flow from the airflow channel to the inside of the sleeve.

13. The inhaler system according to claim 1, wherein the sleeve defines an inner cavity and a portion of the inner cavity has a reduced internal diameter relative to remaining portions of the inner cavity.

14. The inhaler system according to claim 12, wherein the sleeve defines an inner cavity having a reduced inner diameter between the first air inlet zone and the second air inlet zone, and the first air inlet zone has a greater inner diameter than the reduced inner diameter between the first air inlet zone and the second air inlet zone.

15. The inhaler system according to claim 1, wherein the holder further comprises a retaining ring element fixed to the open proximal end of the housing, wherein the retaining ring element retains the sleeve within the inhaler article cavity.

16. The inhaler system according to claim 1, wherein the holder further comprises a marking element separate from the piercing element extending into the inhaler article cavity from the housing inner surface, the marking element configured to mark the outer surface of the inhaler article when the inhaler article is received within the inhaler article cavity.

17. The inhaler system according to claim 16, wherein the marking element is configured to scratch or apply a color to the outer surface of the inhaler article when the inhaler article is received within the inhaler article cavity.

18. The inhaler system according to claim 16, wherein the marking element is configured to mark the outer surface of the inhaler article when the piercing element penetrates the capsule disposed within the inhaler article.

* * * * *